United States Patent [19]
Rajala et al.

[11] Patent Number: 5,711,847
[45] Date of Patent: Jan. 27, 1998

[54] ROTARY ULTRASONIC APPARATUS AND SYSTEM

[75] Inventors: Gregory John Rajala; Thomas David Ehlert, both of Neenah, Wis.

[73] Assignee: Kimberly-Clark Worldwide, Inc., Neenah, Wis.

[21] Appl. No.: 453,533

[22] Filed: May 30, 1995

Related U.S. Application Data

[62] Division of Ser. No. 381,363, Jan. 31, 1995.

[51] Int. Cl.$^6$ ............................................. B29C 65/08
[52] U.S. Cl. ................... 156/580.2; 156/73.1; 425/174.2
[58] Field of Search ......................... 156/73.1, 73.2, 156/73.3, 160, 163, 164, 229, 252, 253, 268, 290, 494, 495, 515, 516, 522, 580.1, 580.2, 581, 582, 583.1; 83/956, 30, 660; 425/174.2; 264/442, 443, 444; 228/1.1, 110.1

[56] References Cited

U.S. PATENT DOCUMENTS

| | | | |
|---|---|---|---|
| 3,217,957 | 11/1965 | Jarvie et al. | 228/1 |
| 3,242,029 | 3/1966 | Deans | 156/380 |
| 3,272,682 | 9/1966 | Balamuth et al. | 156/580.2 |
| 4,747,895 | 5/1988 | Wallerstein et al. | 156/73.3 |
| 4,767,492 | 8/1988 | Fukusima et al. | 156/580.2 |
| 4,975,133 | 12/1990 | Gochermann | 156/73.1 |
| 5,110,403 | 5/1992 | Ehlert | 156/580.1 |
| 5,188,627 | 2/1993 | Igaue et al. | 604/385.2 |

*Primary Examiner*—James Sells
*Attorney, Agent, or Firm*—Mark L. Davis; Tom Wilhelm

[57] ABSTRACT

This invention pertains to apparatus for processing workpieces, including effecting changes in the workpieces by applying ultrasonic energy to the workpieces using novel apparatus and steps for applying the ultrasonic energy to the workpieces. Specifically, an ultrasonic horn and anvil are used to apply ultrasonic energy in a limited amount, to effect change such as cutting in one layer of a workpiece without effecting a corresponding change in the other layers of the workpiece, although some change in the other layers may be tolerated and/or desired. A rotary horn and anvil are taught, with a protuberance on either the horn or the anvil. In use, the horn and anvil preferably rotate cooperatively in close proximity to each other at a nip, and apply pressure and corresponding ultrasonic energy to the workpiece only when the protuberance rotates into the nip, even though ultrasonic energy may be applied uniformly to the ultrasonic horn throughout the rotation of the protuberance. The workpieces may be presented to the horn/anvil combination as contained serially in a web of workpieces passing through the gap at a given speed; the speed of the protuberance being preferably substantially matched to the speed of the web while the protuberance is applying ultrasonic energy to a workpiece, but may differ from the speed of the web when the protuberance is not applying ultrasonic energy to a workpiece.

41 Claims, 10 Drawing Sheets

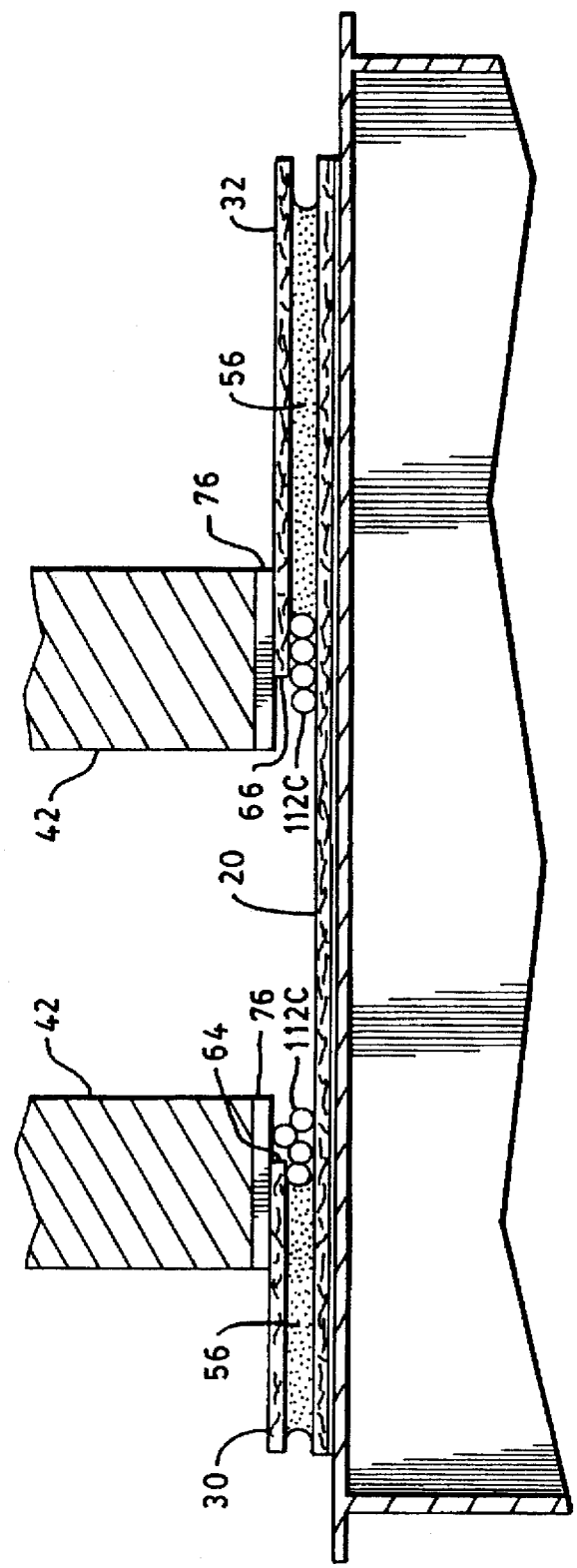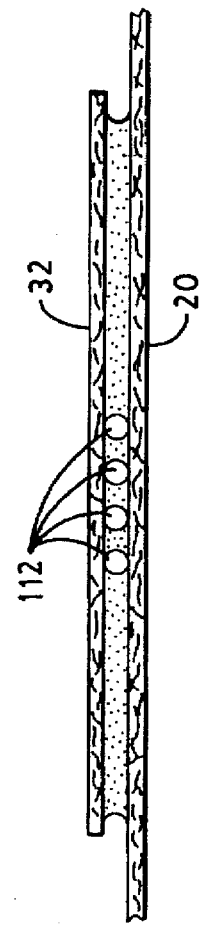

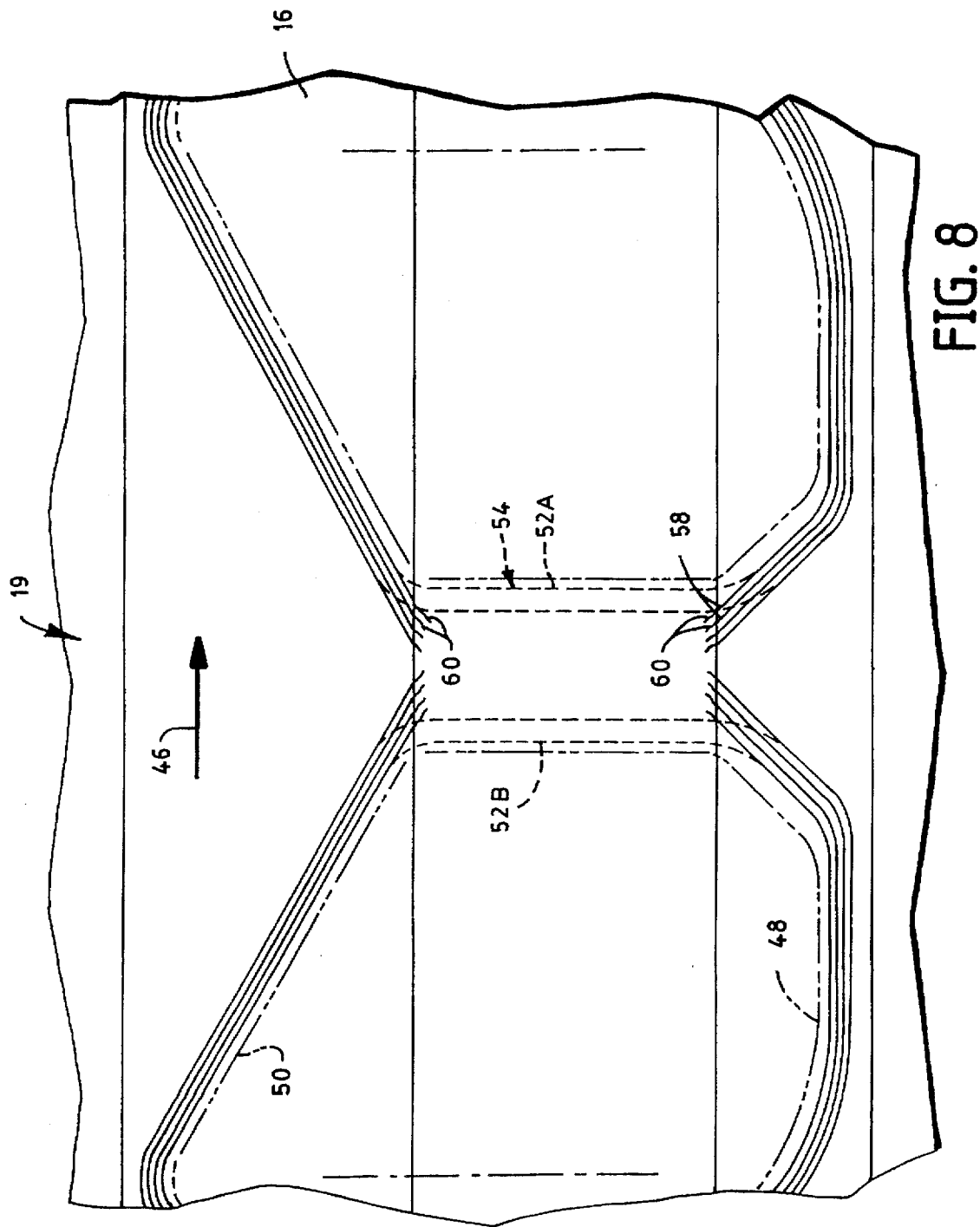

5,711,847

ROTARY ULTRASONIC APPARATUS AND SYSTEM

This is a divisional application of copending Application U.S. Ser. No. 08/381,363, filed on Jan. 31, 1995.

FILED OF THE INVENTION

This invention relates generally to a set of ultrasonic devices comprising an ultrasonic horn and a cooperating anvil. More specifically, it relates to such ultrasonic devices, and methods of using them, which results in control of the ultrasonic processing adapted to selectively effect change in one layer of a multiple layer workpiece without effecting a corresponding change in another layer of the workpiece.

BACKGROUND OF THE INVENTION

The present invention relates to a set of ultrasonic devices, especially rotary ultrasonic devices, and methods of using them.

It is known to apply ultrasonic energy to a rotary ultrasonic horn while rotating the horn against a continuously advancing workpiece to effect a continuous weld line joining two metallic layers of a workpiece, as taught in U.S. Pat. No. 3,217,957 to Jarvie et al.

Similarly, it is known to apply ultrasonic energy to a bell-shaped rotary ultrasonic horn while rotating the horn against a continuously advancing workpiece to effect a continuous weld line joining two plastics layers of a workpiece, as taught in U.S. Pat. No. 3,242,029 to Deans.

Finally, U.S. Pat. No. 5,110,403 Ehlert teaches a high efficiency rotary ultrasonic horn, ostensibly for applying ultrasonic energy to a workpiece along a continuous line of engagement between the workpiece and the radial, or working, surface of the horn.

Ehlert contains little or no discussion of the effect of applying ultrasonic energy to workpieces using his horn. Both Jarvie et al and Deans show a continuous application of the horn to the workpieces, effecting a continuous change (welds) in both layers of the workpiece.

The art is devoid of apparatus and methods for effecting intermittent application of ultrasonics energy to a workpiece for a short, and/or controlled period of time. In addition, the art is devoid of apparatus and methods for effecting a change in one layer of a workpiece at a selected locus while effecting less change, or no change at all, in one or more superposed layers of the workpiece at the selected locus.

It is an object of the invention to provide a method of processing a multiple layer workpiece using ultrasonic energy and thereby effecting a physical change in a first layer of the workpiece without substantially effecting corresponding physical change in a second layer.

It is another object to provide a method of cutting a first interior layer of a multiple layer workpiece without correspondingly cutting at least one other layer of the workpiece.

Another object is to provide methods and apparatus for cutting threads of elastic on the interior of a multiple layer workpiece without cutting any other layer of the workpiece.

It is yet another object to provide a method of applying ultrasonic energy to a workpiece for a short period of time while continuously applying ultrasonic energy to a corresponding ultrasonic horn which applies the energy to the workpiece.

It is still another object to provide rotary ultrasonic apparatus, and methods for applying the apparatus to deliver ultrasonic energy to the workpiece for a short period of time, the apparatus including one or more protuberances on one or both of the horn or the anvil.

It is a further object to provide an ultrasonic system wherein an ultrasonic horn and a cooperating anvil rotate in close proximity with each other, with a gap in between, and closing the gap intermittently to form a nip using a protuberance on one or both of the horn and the anvil.

Still another object is to provide apparatus and methods for controlling the speed of the protuberance such that it substantially matches the speed of advance of the workpiece through the nip while the protuberance is applying ultrasonic energy to the workpiece.

Yet another object is to provide apparatus and methods for controlling the spend of the protuberance such that it substantially matches the speed of the workpiece while the protuberance is applying ultrasonic energy to the workpiece, and differs from the spend of the workpiece while the protuberance is not applying ultrasonic energy to the workpiece.

Another object is to provide a novel rotary ultrasonic horn having a first inner core member having an outer radial surface, and a second activating protuberance secured to and extending outwardly from the outer radial surface, for applying ultrasonic energy to a workpiece for periods of short duration.

A further object is to provide a processing system for processing a series of workpieces in a continuous web, including presenting at least one working protuberance to each workpiece intermittently, such that significant spaces exist between areas of application of the ultrasonic energy in successive workpieces.

SUMMARY OF THE INVENTION

This invention describes apparatus and methods for applying ultrasonic energy to a multiple layer workpiece, and thereby effecting a change, e.g. welding or cutting, in a first layer without effecting a corresponding change in a second layer.

Accordingly, in a first family of embodiments, the invention comprehends a method of processing a multiple layer workpiece having at least first and second layers and an outer surface, and wherein the workpiece is structured such that ultrasonic energy applied to the outer surface at a selected locus of the workpiece can effect physical change in the first layer before effecting a corresponding physical change in at least the second layer at the selected locus, the method comprising applying ultrasonic energy to the outer surface of the multiple layer workpiece at the selected locus, sufficient to effect a physical change in the first layer without effecting corresponding physical change in the second layer.

In some embodiments, the method preferably includes constructing the first layer such that the first layer can concentrate the ultrasonic energy at discrete locations in the first layer, the physical change comprising cutting the first layer at discrete locations, without cutting the second layer. In some embodiments, the method comprehends applying ultrasonic energy with such is power and for such limited time as to effect cutting the first layer and forming a weld at the second layer. In other embodiments, the physical change in the first layer comprises cutting the first layer, and the ultrasonic energy makes no substantial change in any other layer of the workpiece.

Further to the preferred embodiments, the first layer may comprise a plurality of layer elements, wherein the layer elements concentrate the ultrasonic energy in the first layer, and the method comprises applying the ultrasonic energy with sufficient power, for sufficient limited time, and with sufficient force, to effect cutting layer elements in the first layer without cutting the second layer.

The method preferably comprises applying the ultrasonic energy e.g. at the outer surface of the workpiece over a period of about 0.0005 second to about 0.20 second.

The method preferably includes applying ultrasonic energy for an effective period of time through ultrasonic members comprising an ultrasonic horn and a cooperating anvil, and applying the ultrasonic energy for effecting the physical change through a protuberance carried on one of the ultrasonic members, and rotating the ultrasonic member carrying the protuberance, about an axis, as the ultrasonic energy is applied through the protuberance.

Still speaking preferably, the ultrasonic horn may be mounted for rotation about a first axis, with the anvil being mounted for rotation about a second axis, the method including advancing the workpiece at a first speed through a gap between the ultrasonic horn and the anvil, and including substantially matching the surface speed of the protuberance carried on one of the ultrasonic horn and the anvil to the first speed of the workpiece while the ultrasonic energy effects the change in the first layer.

A preferred method including matching surface speed of the protuberance to the surface speed of the workpiece comprehends effecting speed changes in the ultrasonic horn such that (i) the surface speed of the ultrasonic horn substantially matches the surface speed of the workpiece while the protuberance is applying ultrasonic energy to effect change in the first layer, and (ii) the surface speed of the ultrasonic horn substantially differs from the surface speed of the workpiece while the protuberance is not applying the ultrasonic energy to the first layer.

Finally, this first family of embodiments comprehends (i) using an anvil to support the workpiece adjacent an energized and vibrating ultrasonic horn, and thereby creating a close relationship comprising a gap between the ultrasonic horn and the anvil, while moving the workpiece relative to the ultrasonic horn, and applying energy to the ultrasonic horn, and (ii) intermittently closing the gap to form a nip by rotating a protuberance on one of the ultrasonic horn and the anvil through the nip, and thereby applying ultrasonic energy through the protuberance to the workpiece to thereby effect the physical change.

In a second family of embodiments, the invention comprehends a method for processing a series of workpieces to be made into garment-type products, in a continuous web, including using apparatus comprising an ultrasonic subsystem for effectively applying ultrasonic energy to effect a physical change in each workpiece in the continuous web, at periods spaced in time, and at locations in the web. The method comprises the steps of providing a rotary ultrasonic horn having a first axis of rotation and a first circumference comprising a base diameter coincident with a first outer radial surface, the first outer radial surface having a width; providing a rotary anvil having a second axis of rotation, a first length between first and second ends of the rotary anvil, and a second circumference comprising a second base diameter coincident with a second outer radial surface for receiving workpieces to be worked by ultrasonic energy and for cooperating with the rotary ultrasonic horn to apply ultrasonic energy to the workpieces; providing on one of the rotary ultrasonic horn and the rotary anvil at least one working protuberance extending outwardly from the respective one of the first and second outer radial surfaces to form a close relationship comprising a gap between the rotary ultrasonic horn and the rotary anvil; advancing the web, containing the workpieces, through the gap at a first speed; and presenting the at least one working protuberance to each workpiece to be worked, thereby closing the gap to form a nip, applying ultrasonic energy to the workpiece, and correspondingly effecting change in the workpiece.

Preferably, the workpieces comprise first and second layers, the method further comprising effecting change in only the first layer. Preferably, the method effects substantially less change, or no change, in at least one other layer of the workpiece.

Some embodiments comprehend cutting the first layer and forming a weld at the second layer.

In a third family of embodiments, the invention comprehends a method of fabricating a multiple layer product containing fabric and elastic. The method comprises the steps of providing a workpiece including a first layer of fabric; incorporating elastic as one or more threads into the workpiece, with the elastic so disposed in the workpiece as to be susceptible to being changed by ultrasonic energy before the first layer is changed by the ultrasonic energy, the workpiece having an outer surface; and applying ultrasonic energy to the workpiece at a selected locus on the outer surface sufficient to effect a physical change in the elastic without effecting corresponding physical change in the first layer.

The method preferably includes placing the elastic in the workpiece such that the elastic can concentrate the ultrasonic energy at discrete locations, thereby effecting the cutting of the elastic threads, the physical change comprising cutting the first layer, without cutting the second layer.

The method also preferably includes applying the ultrasonic energy over a period of about 0.0005 second to about 0.20 second, especially for an effective period through ultrasonic members comprising an ultrasonic horn and a cooperating anvil, and applying the ultrasonic energy for effecting the physical change through a protuberance carried on one of the ultrasonic members, and rotating the ultrasonic member carrying the protuberance, about an axis, as the ultrasonic energy is applied through the protuberance.

Preferably, the ultrasonic horn is mounted for rotation about a first axis, the anvil being mounted for rotation about a second axis, and the method includes advancing the workpiece at a first speed through a gap between the ultrasonic horn and the anvil, and including substantially matching the surface speed of the protuberance carried on the one of the ultrasonic horn and the anvil to the speed of the workpiece while the ultrasonic energy effects the change in the first layer.

The method comprehends processing the workpiece as a series of workpieces arranged sequentially in a continuous web, carrying the protuberance on the ultrasonic horn, processing each such workpiece with ultrasonic energy using the protuberance, and effecting speed changes in the ultrasonic horn such that (i) the surface speed of the ultrasonic horn substantially matches the surface speed of the workpiece while the protuberance is applying ultrasonic energy to effect change in the elastic, and (ii) the surface speed of the ultrasonic horn substantially differs from the surface speed of the workpiece while the protuberance is not applying the ultrasonic energy to the elastic.

The method may include (i) using an anvil to support the workpiece adjacent an energized and vibrating ultrasonic horn, and thereby creating a close relationship comprising a gap between the ultrasonic horn and the anvil, while moving the workpiece relative to the ultrasonic horn, and applying energy to the ultrasonic horn, and (ii) intermittently closing the gap to form a nip by rotating a protuberance on one of the ultrasonic horn and the anvil through the nip, and thereby applying ultrasonic energy through the protuberance to the workpiece to thereby effect the physical change.

A fourth family of embodiments of the invention comprehends a method of cutting elastic threads in a workpiece comprising a first layer of fabric, and incorporating elastic as one or more threads in the workpiece, the workpiece having an outer surface, and wherein the elastic is so disposed in the workpiece as to be susceptible to being cut by ultrasonic energy before the first layer is cut. The method comprises applying ultrasonic energy to the workpiece at a selected locus on the outer surface sufficient to effect cutting of the elastic without cutting the first layer.

In a fifth family of embodiments, the invention comprehends a rotary ultrasonic horn comprising an axis of rotation and a thickness, the ultrasonic rotary horn comprising a first inner core member having the axis of rotation extending therethrough, the first inner core member having a thickness, a circumference including a base diameter, and an outer radial surface, the outer radial surface having a width, the first inner core member having a center of gravity disposed at the axis of rotation; and a second activating member comprising (i) working protuberance means having a mass, secured to and extending outwardly from the outer radial surface at the base diameter, and (ii) counterbalance means, effective to counterbalance the mass of the working protuberance means, such that the center of gravity of the second activating member is coincident with the axis of rotation.

Preferably, the working protuberance means comprising at least one working protuberance extending outwardly from the outer radial surface a first distance comprising a first height and having a first width, the counterbalance means comprising at least one counterbalancing protuberance extending outwardly from the outer radial surface a second distance comprising a second height and having a second width, the second height being smaller than the first height, the second width being greater than the first width.

Also preferably, at least one working protuberance extends across up to the entire width of the outer radial surface, with the respective working protuberance having a substantially uniform cross-section across the entire width of the outer radial surface.

The first inner core member preferably has a base diameter of about 100 mm to about 200 mm, more preferably about 150 mm, the height of the working protuberance being about 0.5 mm to about 7 mm, more preferably about 4.8 mm, the width of the working protuberance being about 0.5 mm to about 7 mm, more preferably about 4.8 mm.

In a sixth family of embodiments, the invention includes an ultrasonics system, comprising a rotary ultrasonic horn having a first axis of rotation, the rotary ultrasonic horn comprising a first inner core member having the first axis of rotation extending therethrough, the first inner core member having a thickness, a first circumference comprising a base diameter coincident with a first outer radial surface, the first outer radial surface having a width, the first inner core member having a center of gravity disposed at the first axis of rotation, the rotary ultrasonic horn further comprising a second activating member comprising working protuberance means having a mass contiguous with and extending outwardly from the first outer radial surface at the base diameter; and a rotary anvil having a second axis of rotation, a second circumference defining a second outer radial surface for receiving a workpiece to be worked by ultrasonic energy, and for cooperating with the rotary ultrasonic horn to form a close relationship comprising a gap between the rotary ultrasonic horn and the rotary anvil, and thereby to apply force to a workpiece being worked by ultrasonic energy.

Preferably, the rotary ultrasonic horn includes counterbalance means extending outwardly from the first outer radial surface, effective to counterbalance the mass of the working protuberance means, such that the center of gravity of the second activating member is essentially coincident with the first axis of rotation.

The working protuberance means preferably comprises at least one working protuberance extending outwardly from the first outer radial surface a first distance comprising a first height and having a first width, the counterbalance means comprising at least one counterbalancing protuberance extending outwardly from the first outer radial surface a second distance comprising a second height and having a second width, the second height being smaller than the first height, the second width being greater than the first width.

Preferably, the working protuberance means comprises at least one working protuberance extending across up to the entire width of the outer radial surface, with the working protuberance having a substantially uniform cross-section across up to the entire width of the outer radial surface.

Preferably, the base diameter of the first inner core member is about 100 mm to about 200 mm, more preferably about 150 mm, the height of the working protuberance is about 0.5 mm to about 7 mm, more preferably about 4.8 mm, and the first width of the first working protuberance is about 0.5 mm to about 7 mm, more preferably about 4.8 mm.

In a seventh family of embodiments, the invention comprehends a rotary ultrasonics system, comprising a rotary ultrasonic horn, having a first axis of rotation, and a first outer radial surface for applying ultrasonic energy to a workpiece to be worked; and a rotary anvil having a second axis of rotation, a circumference including a base diameter and a second outer radial surface generally coincident with the base diameter for receiving a workpiece thereon and transporting the workpiece, and for cooperating with the rotary ultrasonic horn to apply energy to the workpiece being worked, the rotary anvil comprising at least one working protuberance on the second outer radial surface, extending outwardly from the base diameter, for working the workpiece using ultrasonic energy supplied by the ultrasonic horn, the length of the working protuberance preferably extending along the length of the anvil, and being shorter than the length of the anvil.

In an eighth family of embodiments, the invention comprehends a processing system for processing workpieces in a continuous operation, the processing system comprising an ultrasonic subsystem, the ultrasonic subsystem comprising (i) a rotary ultrasonic horn having a first axis of rotation, the rotary ultrasonic horn comprising a first inner core member having the first axis of rotation extending therethrough, the first inner core member having a thickness, a first circumference comprising a base diameter coincident with a first outer radial surface, the first outer radial surface having a width, the first inner core member having a center of gravity essentially coincident with the first axis of rotation, the rotary ultrasonic horn further comprising a second activating member comprising working protuberance means having a mass contiguous with and extending outwardly from the first outer radial surface at the base diameter; and (ii) a rotary anvil having a second axis of rotation, a second circumference defining a second outer radial surface for receiving a workpiece to be worked by ultrasonic energy, and for cooperating with the rotary ultrasonic horn to form a close relationship comprising a gap between the rotary ultrasonic horn and the rotary anvil, and thereby to apply force to a workpiece being worked by ultrasonic energy; and means for advancing a web, containing workpieces to be worked, through the gap at a first speed.

Preferably, the rotary ultrasonic horn further comprises counterbalance means effective to counterbalance the mass of the working protuberance means such that the center of gravity of the rotary ultrasonic horn is essentially disposed at the first axis of rotation.

In preferred embodiments, the working protuberance means comprises a working protuberance on the rotary ultrasonic horn, and includes drive means for driving the rotary ultrasonic horn and thereby substantially matching the surface speed of the working protuberance with the first speed when the working protuberance applies ultrasonic energy to the workpiece, preferably by using a set of noncircular gears adapted to effect speed changes in the ultrasonic horn such that (i) the surface speed of the ultrasonic horn substantially matches the surface speed of the rotary anvil while the protuberance is applying ultrasonic energy to work the workpiece, and such that (ii) the surface speed of the ultrasonic horn substantially differs from the surface speed of the anvil while the protuberance is not applying ultrasonic energy to the workpiece.

Finally, in a ninth family of embodiments, the invention comprehends a processing system, for processing a series of workpieces comprising garment-type products in a continuous web, the processing system including an ultrasonic subsystem for applying ultrasonic energy to effect physical change in each workpiece in the continuous web, at periods spaced in time, and at locations in the web. The ultrasonic subsystem comprises a rotary ultrasonic horn having a first axis of rotation, a first circumference comprising a base diameter coincident with a first outer radial surface, the outer radial surface having a width; a rotary anvil having a second axis of rotation, a first length between first and second ends of the rotary anvil, a second circumference comprising a second base diameter coincident with a second outer radial surface for receiving workpieces to be worked by ultrasonic energy and for cooperating with the rotary ultrasonic horn to apply ultrasonic energy to workpieces to be worked by ultrasonic energy; one of the rotary ultrasonic horn and the rotary anvil having at least one working protuberance extending outwardly from the respective one of the first and second outer radial surfaces to form a close relationship comprising a gap between the rotary ultrasonic horn and the rotary anvil; means for advancing the web, containing the workpieces, through the gap at a first speed; and means for effectively presenting the at least one working protuberance to each workpiece to be worked, to thereby close the gap to form a nip, apply ultrasonic energy to the workpiece, and correspondingly effect change in the workpiece.

Preferably, the working protuberance has a length, shorter than the length of the anvil, the system being adapted to process a workpiece comprising first and second layers, a width, and an outer surface, the physical change preferably comprising cutting the first layer without cutting any portion of any other layer of the workpiece.

It is also preferred that the working protuberance have a second length, the system being adapted to process a workpiece comprising (i) a first layer, (ii) a second layer, and (iii) a width, the second length of the working protuberance being shorter than the width of the workpiece to be worked.

In preferred embodiments, the working protuberance is disposed on the rotary ultrasonic horn, and the processing system comprises drive means for driving the rotary ultrasonic horn and thereby substantially matching the surface speed of the working protuberance with the speed of the workpiece when the working protuberance applies ultrasonic energy to the workpiece.

Preferred dimensions for the working protuberance are height, measured from the corresponding the outer radial surface, of about 0.5 mm to about 7 mm, more preferably about 4.8 mm, and a width of about 0.5 mm to about 7 mm, more preferably about 4.8 mm.

BRIEF DESCRIPTION OF THE DRAWINGS

The present invention will be more fully understood and further advantages will become apparent when reference is made to the following detailed description of the invention and the drawings, in which:

FIG. 6 is a fragmentary cross-section of the web taken at 6—6 of FIG. 5.

FIG. 7 is a cross-section of the web, and corresponding ultrasonic horn and anvil, taken at 7—7 of FIG. 3.

FIG. 8 is a top view of the portion of one workpiece incorporating elastic after the elastic threads have been cut at the crotch portion by the ultrasonic apparatus of the invention.

DETAILED DESCRIPTION OF THE ILLUSTRATED EMBODIMENTS

The following detailed description is made in the context of fabricating disposable-type garments such as diapers, training pants, feminine care products, feminine care and incontinence garments and the like.

Figure 1:
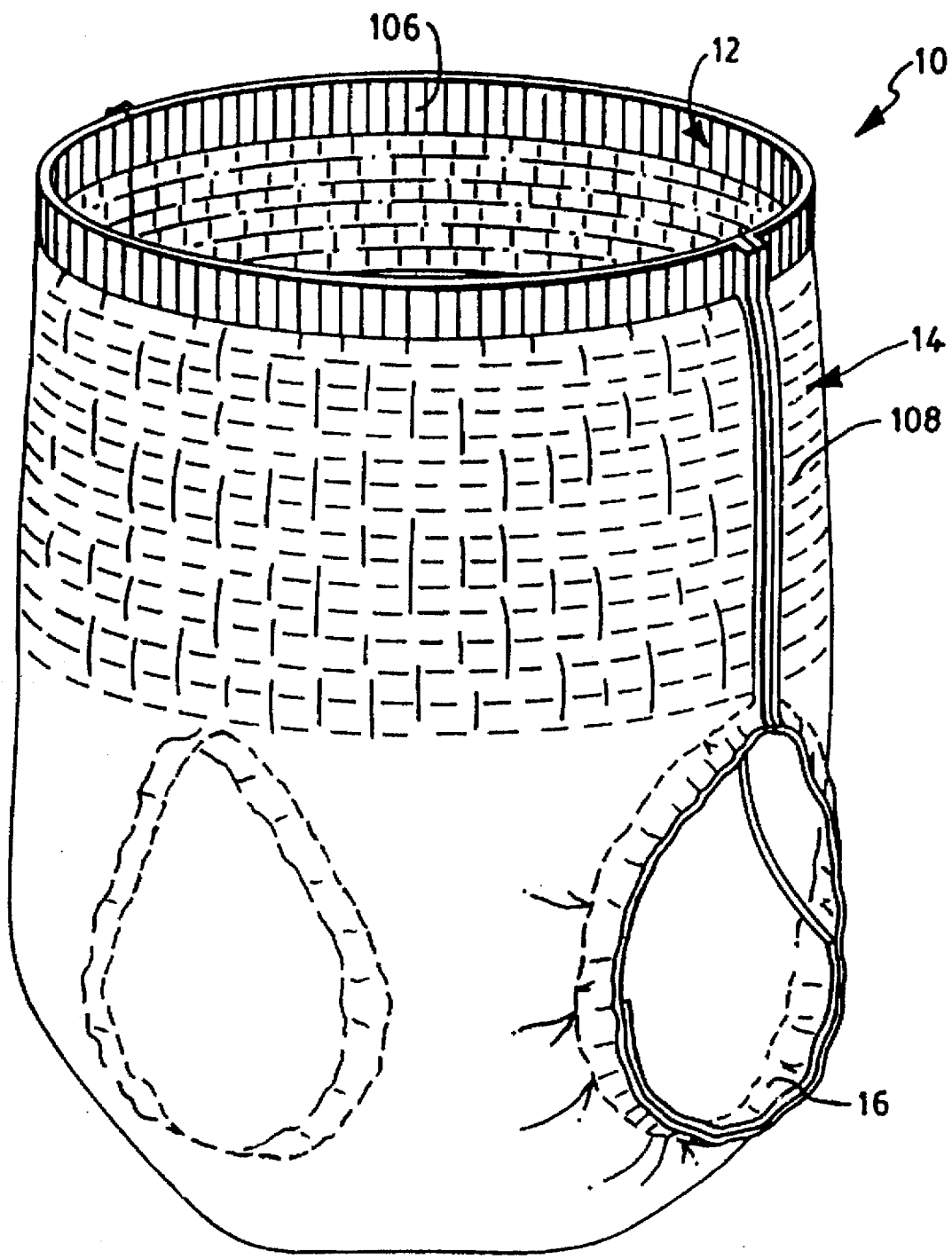
FIG. 1 is a perspective view of a disposable garment such as diapers, training pants, feminine care and incontinence garments, feminine care pads, and the like which may be made using methods and apparatus of this invention.

Except for the novel features of the garment resulting from the novel methods and apparatus disclosed herein, it is generally known to make disposable-type garments such as the garment 10 shown in FIG. 1. Such garments typically comprise an assemblage of one or more layers of woven or non-woven fabric and/or poly films. Elastic is typically also incorporated into the assemblage. Elastic may be used at the waist 12, in the body portion 14 of the garment, and around the leg openings 16.

Materials suitable for use as the elastics include a wide variety, but not limited to, of elastic threads, yarn rubber, flat rubber (e.g. as bands), elastic tape, film-type rubber, polyurethane, and, tape-like elastomer, or foam polyurethane or formed elastic scrim. Each elastic may be unitary, multipart, or composite in construction. Threads or ribbons, where used, may be multiple and may be applied as a composite. The multiple layer elements are substantially round in cross-section, as shown in FIG. 7, to effectively concentrate the ultrasonic energy and thereby to effect severing. The elastomerics used in the elastics may be latent and nonlatent.

Figure 2:
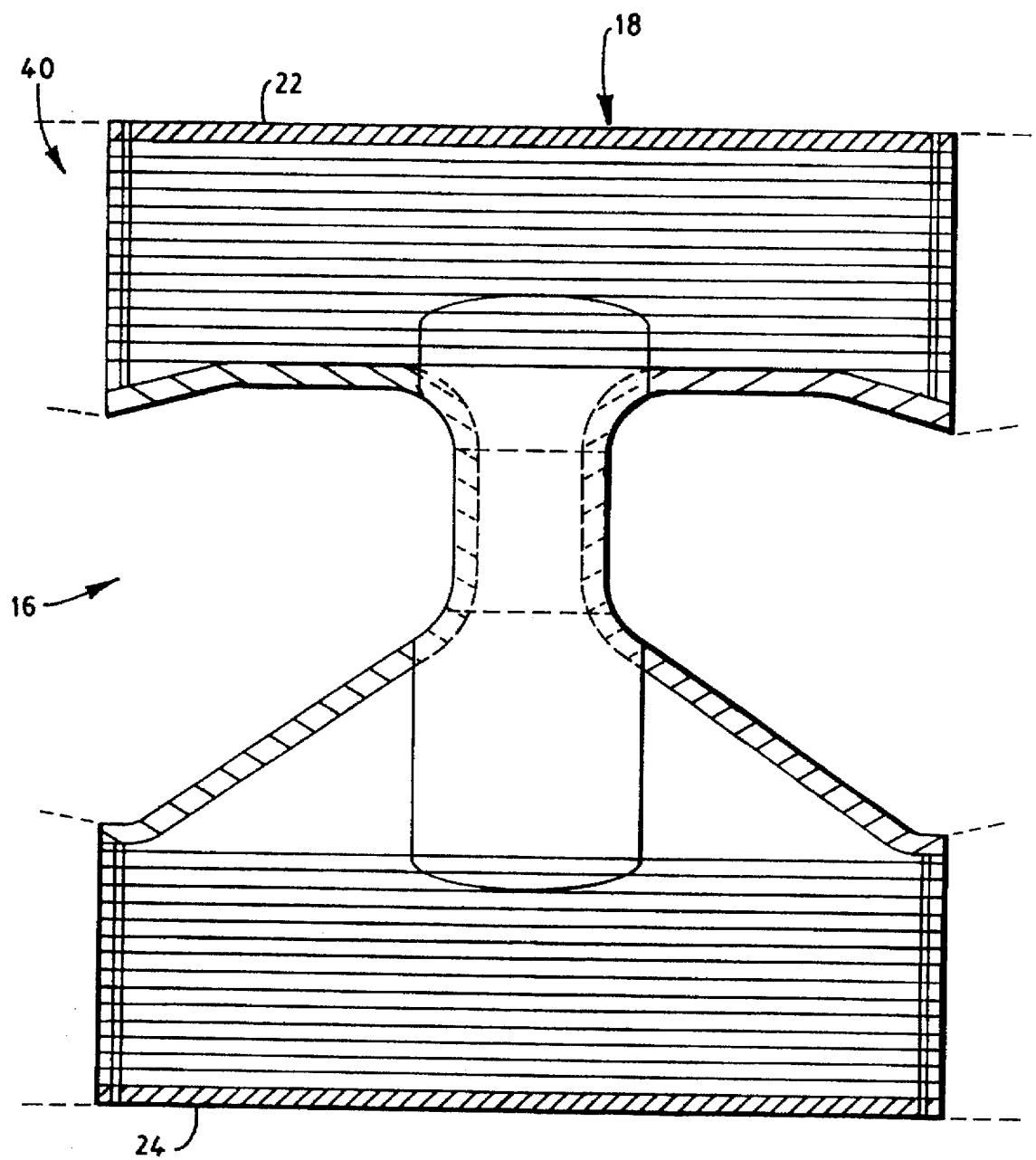
FIG. 2 is a top view of a finished garment blank, as a finished workpiece in a continuous web, from which the garment of FIG. 1 can be made.

In this invention, as in most such processes for fabricating the garment as at 10, a blank 18 such as that shown in FIG. 2 is first made as part of a continuously processed web of material.

Figure 5:
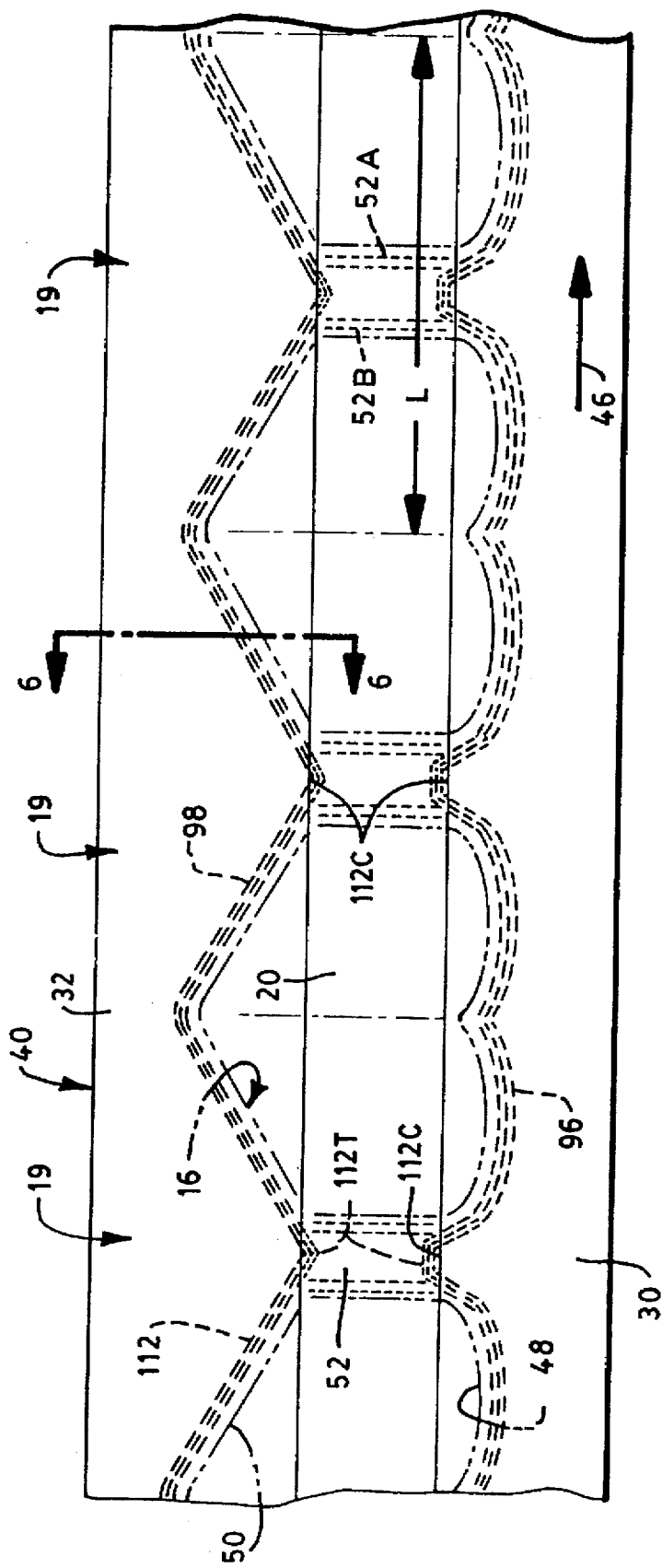
FIG. 5 is a top view of a fragment of the continuous web after the elastic has been incorporated into the web, showing three workpieces, comprising three garment blanks, and is taken at 5—5 of FIG. 3.

Methods and apparatus for incorporating elastic at the leg openings 16 has been the subject of a significant amount of research work and development work. Where, as indicated in FIGS. 2, 5, and 8, the front-to-back dimension of the blank 18 is disposed transverse to the web, no suitable means has been propounded for incorporating the elastic about the leg openings 16 while advancing the processing web at a generally continuous speed.

U.S. Pat. No. 5,188,627 Igaue et al. teaches incorporating front and back leg elastics, including the crotch portion, by bonding stretched elastic along shallow arcuate paths along the leg openings, and stretching the elastic across the crotch without bonding, in a transversely oriented processing operation. When the stretching of the elastic is subsequently relaxed, the elastic extending across the crotch will tend to draw the opposing edges of the crotch together, and thus to cause the material in the crotch to bunch up.

The methods and apparatus of this invention can be used to produce disposable-type garments in continuous, cross-web orientation, including incorporating front and back log elastics while avoiding even the potential for elastic to cause bunching of material in the crotch portion.

Figure 3:
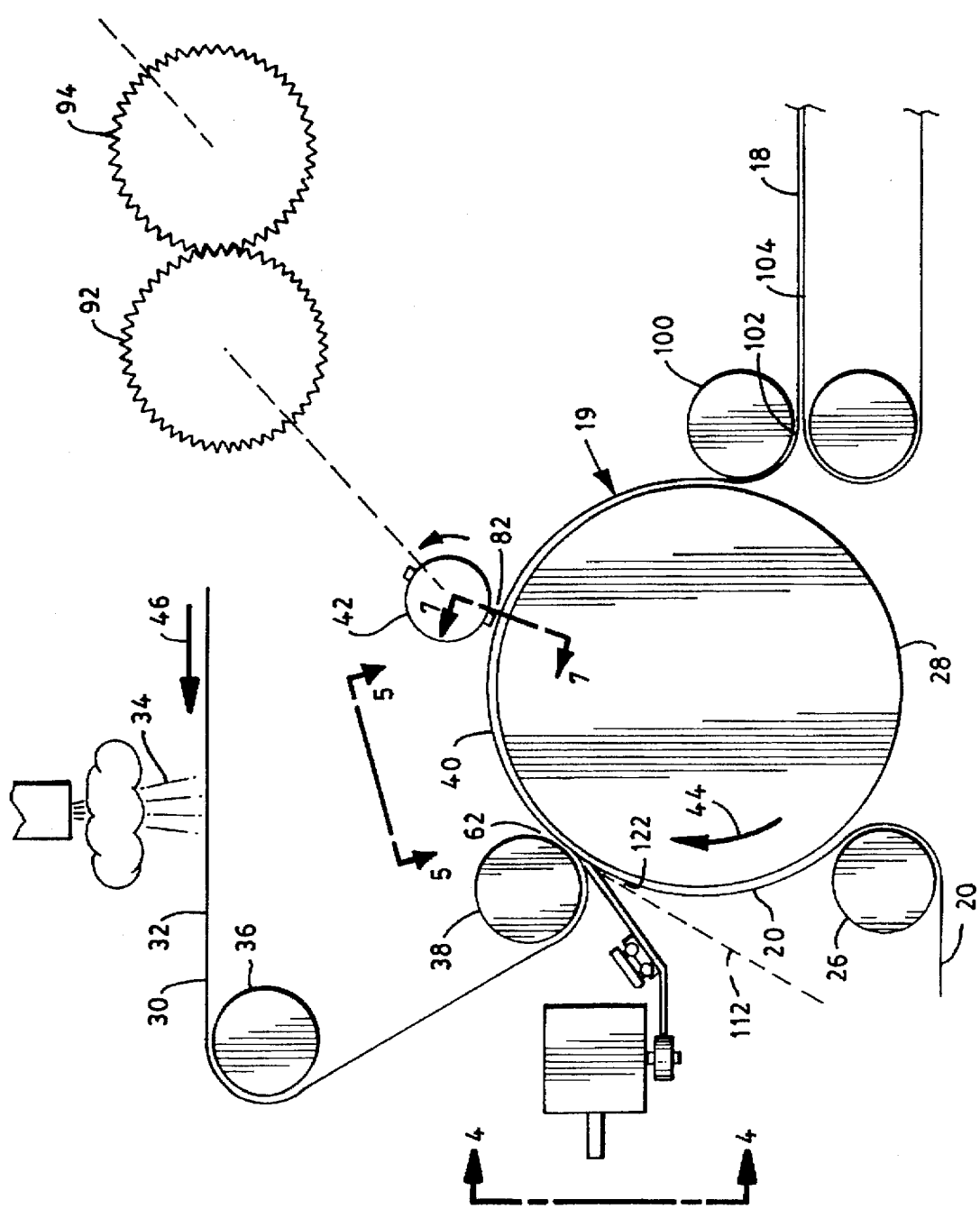
FIG. 3 is a side elevation of one section of the processing apparatus used to make the garment blank of FIG. 2 in a continuous web, and which incorporates ultrasonics system and methods of this invention.

FIG. 3 in general shows a side elevation of a portion of the processing equipment of a preferred processing line of the invention. The portion of the processing line shown in FIG. 3 includes steps and apparatus for incorporating the elastic into the workpieces 19 in the continuous web, which become the blanks 18 when the workpieces 19 are severed from the web.

Referring to FIG. 3, a base web 20 having a width, extending at least from the front waist edge 22 (FIG. 2) of the garment blank 18 to the back waist edge 24 is drawn into the elements of the processing system shown, around turning roll 26, and is thence incorporated onto the anvil roll 28, which turns in the direction indicated by arrow 44. Direction of movement of the front and back cover web through the system is shown by the arrows 46.

Front and back cover webs 30 and 32 are drawn into the processing system in side-by-side relationship, under adhesive spray 34, about turning roll 36, then pass around turning roll 38 and are pressed against the base web 20, where the layer of adhesive 56 (FIG. 7) bends the cover webs 30, 32 to the base web 20.

Figure 4:
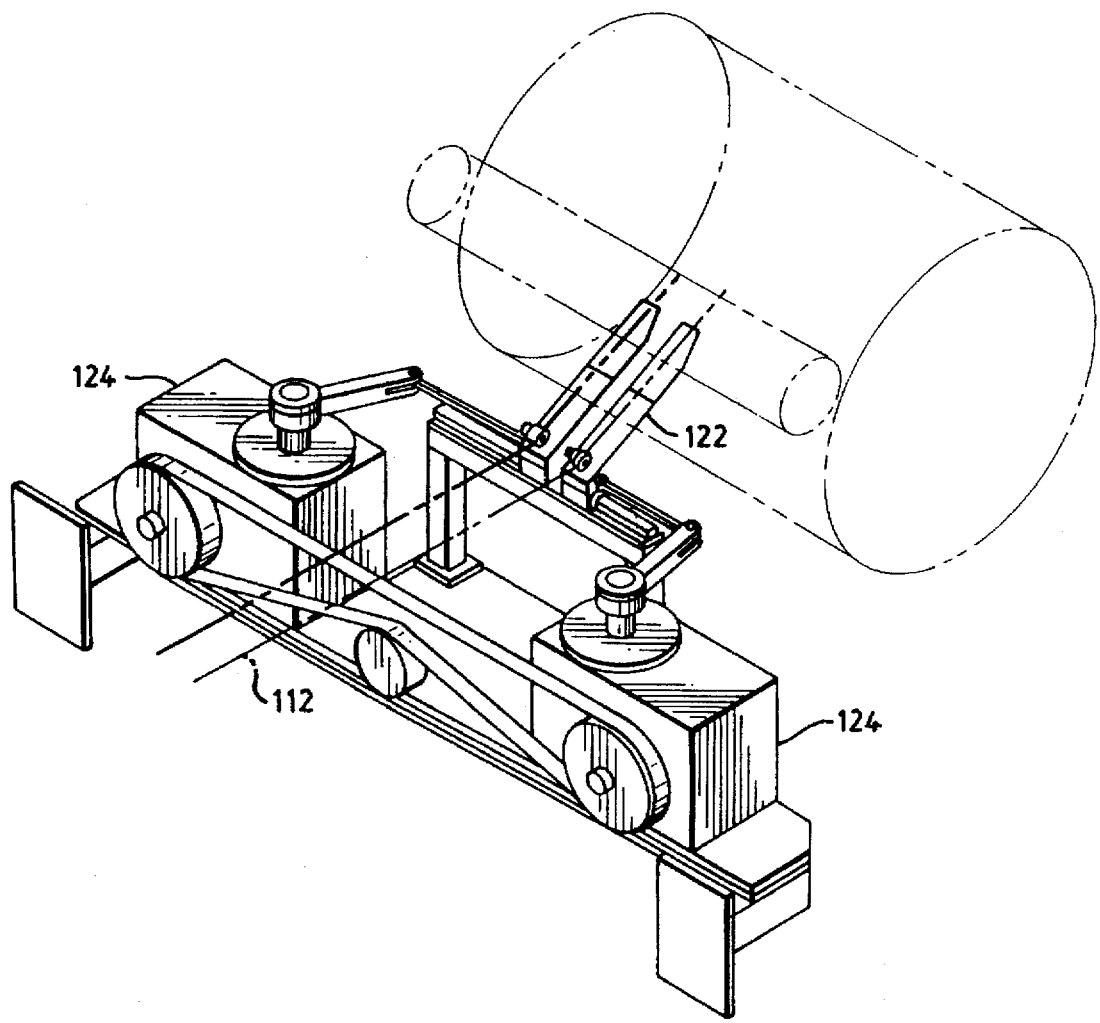
FIG. 4 is a perspective view of apparatus for incorporating elastic into the continuous web, taken at 4—4 of FIG. 3.

As the cover webs 30, 32 are adhered to the base web 20 at the nip 62 between turning roll 38 and anvil roll 28, stretched threads of elastic 112 are fed into the nip by thread guides 122. See also FIG. 4. In preferred embodiments, the threads of elastic are stretched ranging from minimal stretch to about 300%, preferably about 150%, as they are guided into nip 62 by thread guides 122. As seen in FIG. 4, the thread guides 122 are mounted to guide controllers (cam driven or servo driven linkages) 124 which move transverse to the webs in a desired sequence of transverse movements to thus position the threads of elastic in the webs in a desired pattern.

In the embodiment illustrated in FIGS. 4–8, each thread of elastic 112 is generally fed into the nip between the base web 20 and one of the cover layers 30, 32. However, as the leading edge 52A of the crotch portion 54 enters the nip 62, the transverse movement of thread guides 122 causes the thread to be placed on the base web at the nip 62 at a locus disposed transverse to the respective cover web, namely between the inner edges 64, 66 of front cover web 30 and back cover web 32, respectively, and thus not entrapped between the base web 20 and the respective cover web. After the web has progressed until the opposing and trailing edge 52B of the crotch portion is at the nip, movement of the thread guides 122 again causes the thread 112 to be placed on the base web in a locus disposed between the base web 20 and the respective cover web. The thread guides 122 are, of course, simultaneously placing as many threads of elastic 112 as desired at both the front and back portions 48, 50 of the leg openings.

FIG. 5 shows the combined web 40, including base web 20, cover webs 30 and 32, and threads of elastic 112 in a desired pattern outlining front portion 48 and back portion 50 of the leg openings 16, as the combined web 40 progresses from the nip 62 of turning roll 38 and anvil roll 28 toward the ultrasonic horn 42. The leg openings 16 are cut in the blanks 18 in steps subsequent to those illustrated in the drawings. Accordingly, the general outlines only of the leg openings 16 are shown in dashed representation in FIGS. 5 and 8.

As illustrated in FIG. 5, the common dashed lines labelled 112 represent the threads of elastic disposed between cover webs 30, 32 and the base web 20. FIG. 6 illustrates the threads of elastic 112 as entrapped between the base web 20 and the back cover web 32. The shorter dashed lines labelled 112T represent the paths of the threads of elastic 112 as positioned by the thread guides 112 at the nip 62. However, since the adhesive is placed on the cover webs, not the base web, and since the threads of elastic are not disposed under either cover web 30, 32 at the crotch portion, the threads of elastic are not bonded to any web across the crotch portion 52.

Accordingly, as soon as the threads emerge from being held under the pressure at the nip 62, they retract along the respective inner edges 64, 66 of the front and back cover webs, respectively. As a result, the threads of elastic crossing the crotch portion 54 between respective front portions 48, or respective back portions 50 of a leg opening, are generally bunched together along the inner edges 64, 66 of the respective cover webs, as seen in FIG. 7. The threads of elastic 112 along each inner edge 64, 66 thus form a loose rope-like arrangement between the loci where the respective threads emerge from the edge of the adhesive layer 56 adjacent the leading edge 52A of the crotch portion and the loci where the threads re-enter the adhesive layer adjacent the trailing edge 52B of the crotch portion.

To the extent the side edge of the adhesive layer 56 on cover webs 30, 32 terminates short of the inner edge 64 or 66 of the respective cover web, the threads of elastic tend to collect under the edge of the respective cover web, between the cover web and the base web. Three of the four threads are thus shown between the base web and the back cover web 32 in FIG. 7. However, where the edge of the adhesive pattern closely approaches the inner edge of the cover web, the threads of elastic cannot all fit in the preferred orientation under the cover web, whereupon they bunch up, which can include some random stacking of the threads on top of each other as shown in FIG. 7 at the inner edge 64 of the front cover web 30.

FIG. 7 thus illustrates the position of the portions of the threads of elastic 112C traversing the crotch portion 54 of the blank just prior to being cut by ultrasonic horn 42. The portions 112C of the threads are also seen in FIG. 5. As the workpieces in the web are processed at the ultrasonic horn 42, and as discussed in more detail hereinafter, the cross-crotch elastics are cut by the ultrasonic energy applied by the ultrasonic horn.

When the cross-crotch elastics are thus cut, each thread retracts to the locus 58 where the respective thread of elastic emerges from the edge of the adhesive layer 56, and thus the bonding action of the adhesive layer. Thus the respective threads of elastic are completely severed as shown in FIG. 8, while the base layer and the cover layer remain unsevered. The retracted threads, e.g. after cutting, thus have free ends 60. Accordingly, as each workpiece 19 exits the cutting step at ultrasonic horn 42 as illustrated in FIG. 8, the log elastics extend, between base layer 20 and the corresponding cover layer 30 or 32, along the front and back portions 48, 50 respectively of each log opening 16, and to each edge 52 of the corresponding crotch. However, since the cross-crotch elastics have been cut at the crotch, the elastics do not extend across the crotch.

Key to success in fabricating the blank 18 is the inventors' discovery of novel apparatus and methods for controlling the amount of ultrasonic energy being applied by the ultrasonic horn 42, and thus creating a control system for cutting the threads of elastic 112, the threads 112 in a sense constituting a separate layer intermediate the base web and the respective cover web, without cutting or otherwise significantly harming the base web or the cover web. While it is known to use ultrasonic energy to cut, or weld together, all layers/webs in a multiple layer structure, applicants teach herein apparatus and methods which enable cutting the threads of elastic without cutting or welding the base web or the respective cover web. In an alternative method of the invention, the threads of elastic are cut, and simultaneously the respective cover web is welded to the base web.

Up to this point, the discussion has focused on the results achieved by using the apparatus and methods of the invention. Following is a more specific discussion of the preferred embodiments of specific apparatus and methods used to achieve the desired results.

Figure 10:
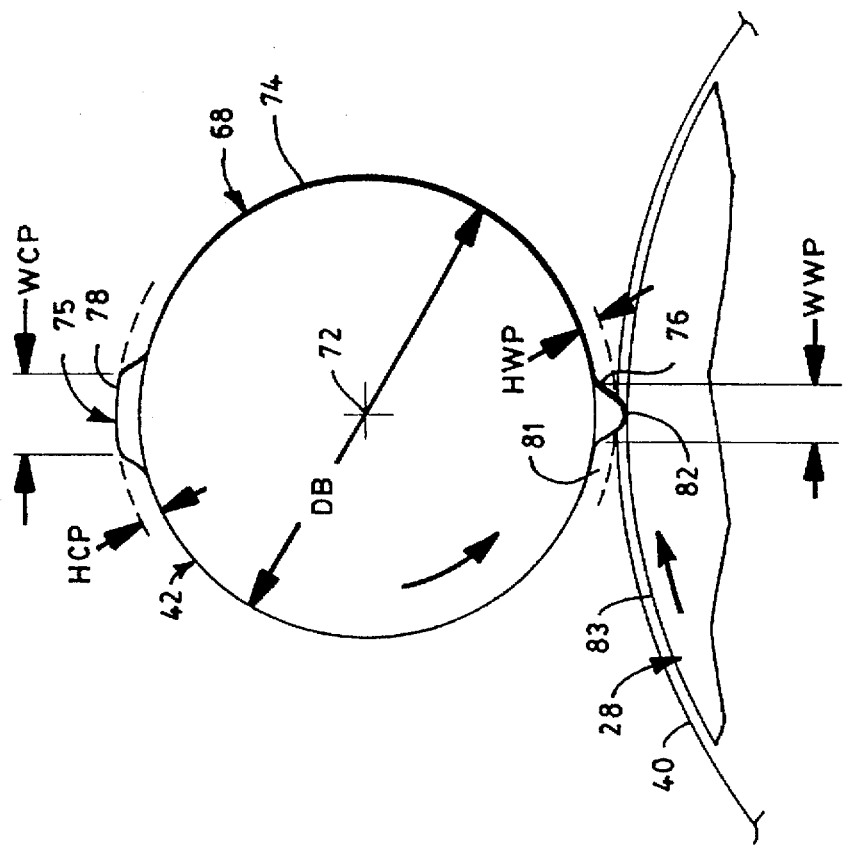
FIG. 10 is a cross-section of the ultrasonic horn taken at 10—10 of FIG. 9, with addition of representative section of the respective anvil roll.
Figure 9:
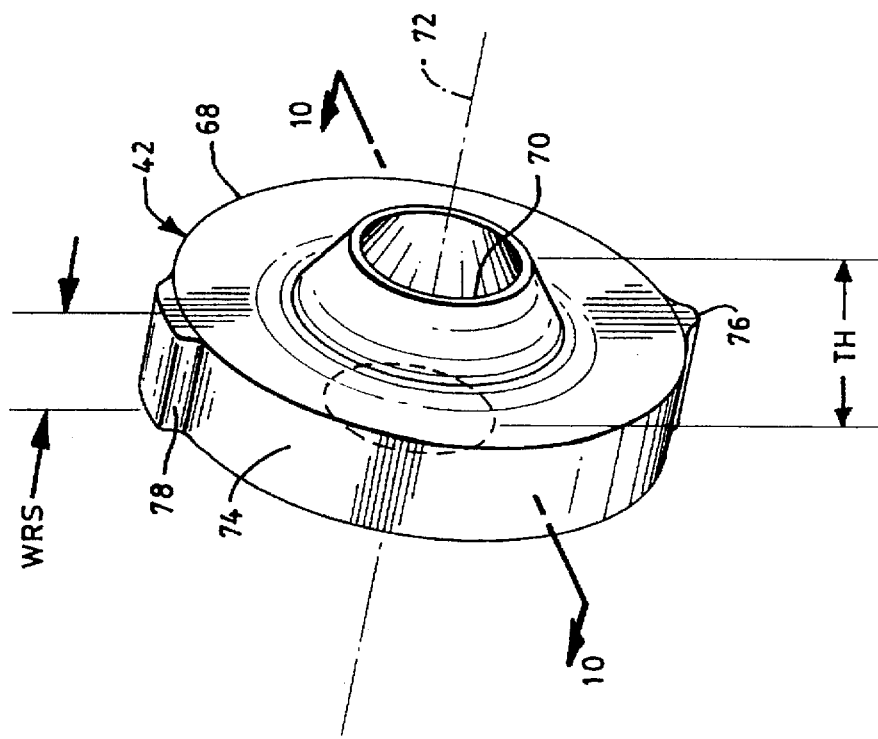
FIG. 9 is a perspective view of a novel ultrasonic horn of this invention.

Referring now to FIGS. 9 and 10, a suitable ultrasonic horn 42 is a rotary ultrasonic horn such as that taught in U.S. Pat. No. 5,110,403 to Ehlert, modified as discussed hereinafter. U.S. Pat. No. 5,110,403 is herein incorporated by reference-for its teaching of the general structure and general use of such rotary ultrasonic horn.

The rotary ultrasonic horn 42 incorporates the rotary horn taught in U.S. Pat. No. 5,110,403 as an inner core member 68. Ultrasonic displacement of horn 42, and thus of inner core member 68, is accomplished by means of a separate element comprising an ultrasonic piezoelectric transducer. The ultrasonic transducer produces mechanical vibration at ultrasonic frequency, thus mechanical ultrasonic energy, and is attached to ultrasonic horn 42 through appropriate booster apparatus, to thereby cause mechanical displacement of the ultrasonic horn at ultrasonic frequency. The ultrasonic horn thus receives mechanical ultrasonic energy at axis of rotation 72. The inner core member 68 thus includes a hub area 70, an axis of rotation 72 extending through the hub area, an overall thickness "TH," a base diameter "DB," and an outer radial surface 74. The center of gravity of inner core member 68 is disposed at, and generally corresponds with, the axis of rotation 72.

Rotary ultrasonic horn 42 further comprises an activating member 75, including a working protuberance 76 and a counterbalancing protuberance 78. Referring now especially to FIG. 10, the protuberances 76 and 78 are shown with stippled shading in order to highlight their presence. In addition, the outline of a phantom (non-existent in that location) working protuberance is shown in dashed outline superposed on the counterbalancing protuberance 78 in order to show the comparative differences in the structures of the two protuberances, and the comparative cooperations of the protuberances and the underlying anvil roll 28.

The purpose of the working protuberance 76 is to perform the work of selectively cutting the elastic threads at the crotch, portions; while, only as desired, at the same time forming welds or cuts in the cover web and/or the base web. In some embodiments, the working protuberance of ultrasonic horn 42 can physically contact back cover web 32 without directly physically contacting the threads of elastic 112C as shown in FIG. 7.

By comparison, the purpose of the counterbalancing protuberance is to provide a mass that counterbalances the mass of the working protuberance. Preferably, the counterbalancing protuberance is effective to project the center of gravity of the combination of working protuberance and counterbalancing protuberance (e.g. activating member 75) onto the axis of rotation 72, preferably superposed on the center of gravity of the inner core member 68, thus maintaining the center of gravity of the horn at the axis of rotation.

As shown in FIG. 9, the counterbalancing protuberance 78 generally extends along up to the entire width "WRS" of the radial surface. Similarly, the working protuberance also typically extends along up to the entire width "WRS" of the radial surface. Outer radial surface 74 has a cylindrical shape continuously extending about the circumference of inner core member 68 as shown in FIGS. 9 and 10. Thus outer radial surface 74 comprises a cylindrical outer radial surface.

Working protuberance 76 has a first height "HWP" and a first width "WWP." Counterbalancing protuberance 78 has a second height "HCP" and a second width "WCP." As a general principle, the height "HCP" of the counterbalancing protuberance 78 is less than the height "HWP" of the working protuberance 76.

The specific height and width of the working protuberance, and its corresponding counterbalancing protuberance, vary according to the working environment in which the activating member will be used. Applicant has experimented with the invention using base web 20 and cover webs 30, 32 at 24 grams per square meter (gsm) each, spunbonded polypropylene. The elastic was Lycra® elastic threads at 940 decitex. The inner core member 68 of the rotary ultrasonic horn used was about 150 mm in diameter. Given those working conditions, the working protuberance has preferred height "HWP" of 4.8 mm, and had a preferred width "WWP" of 4.8 mm. A preferred range of heights "HWP" for this working environment is about 0.5 mm to about 7 mm. A preferred range of widths "WP" for this working environment is also about 0.5 mm to about 7 mm.

The preferred height "HCP" of the counterbalancing protuberance 78 depends on the height "HWP" of the working protuberance, with the height "HCP" preferably being about half the height of the working protuberance. Accordingly, in the above working environment, and given a height of 4.8 mm for "HWP," the preferred height "HCP" for the counterbalancing protuberance is about 2.4 mm.

Once the height of the counterbalancing protuberance has been determined, the width "WCP" of the counterbalancing protuberance is preferably determined by calculating the width necessary to provide the mass required to counterbalance the mass of the working protuberance, and thereby position the center of gravity of the combination of the spaced working protuberance and counterbalancing protuberance (e.g. the activating member 75) on the axis of rotation 72. Where, for example, the height "HCP" of the counterbalancing protuberance is about half the height of the working protuberance, the width "WCP" is about twice the width "WWP" of the working protuberance.

The working protuberance and the counterbalancing protuberance each preferably have a length, and substantially uniform cross-section, extending the full width "WRS" of the outer radial surface 74, which length is, as shown in FIG. 9, substantially less than the overall length "TH" of the anvil roll between its opposing ends. The working protuberance can be shorter than the width "WRS." However, it generally is not longer than the width of the outer radial surface. Similarly, the counterbalancing protuberance can be shorter than the width of the radial surface, as desired, so long as the mass balance is achieved, and the center of gravity is disposed on the axis of rotation.

The significance of the center of gravity being on the axis of rotation is generally two-fold. First, such properly positioned center of gravity assists in maintaining the mechanical rotational stability of the horn as it rotates about its axis 72. Second, maintaining the center of gravity at the same locus as that of the inner core member 68 contributes to the ultrasonic efficiency of the horn wherein the inner core member 68 alone was designed for efficient transfer of ultrasonic energy.

Referring now to FIG. 10, in the example illustrated herein, the outer radial surface 74 of horn 42 has a width "WRS" of about 50 mm. In the embodiments illustrated, the outer radial surface is biased against the anvil roll 28 with a force of e.g. 40–450 newtons across the 50 mm width "WRS," and against an absolute stop 80 (see FIG. 11) set to provide zero clearance, and thus to provide a nip 82 between the horn 42 and the anvil roll 28, when the working protuberance 76 is rotated against the anvil roll 28 as shown in FIG. 10. The biasing force is somewhat dependent on the working environment, including the structure of the workpieces 19. Accordingly, the above-recited force is not limiting, and is intended to be illustrative only.

Figure 11:
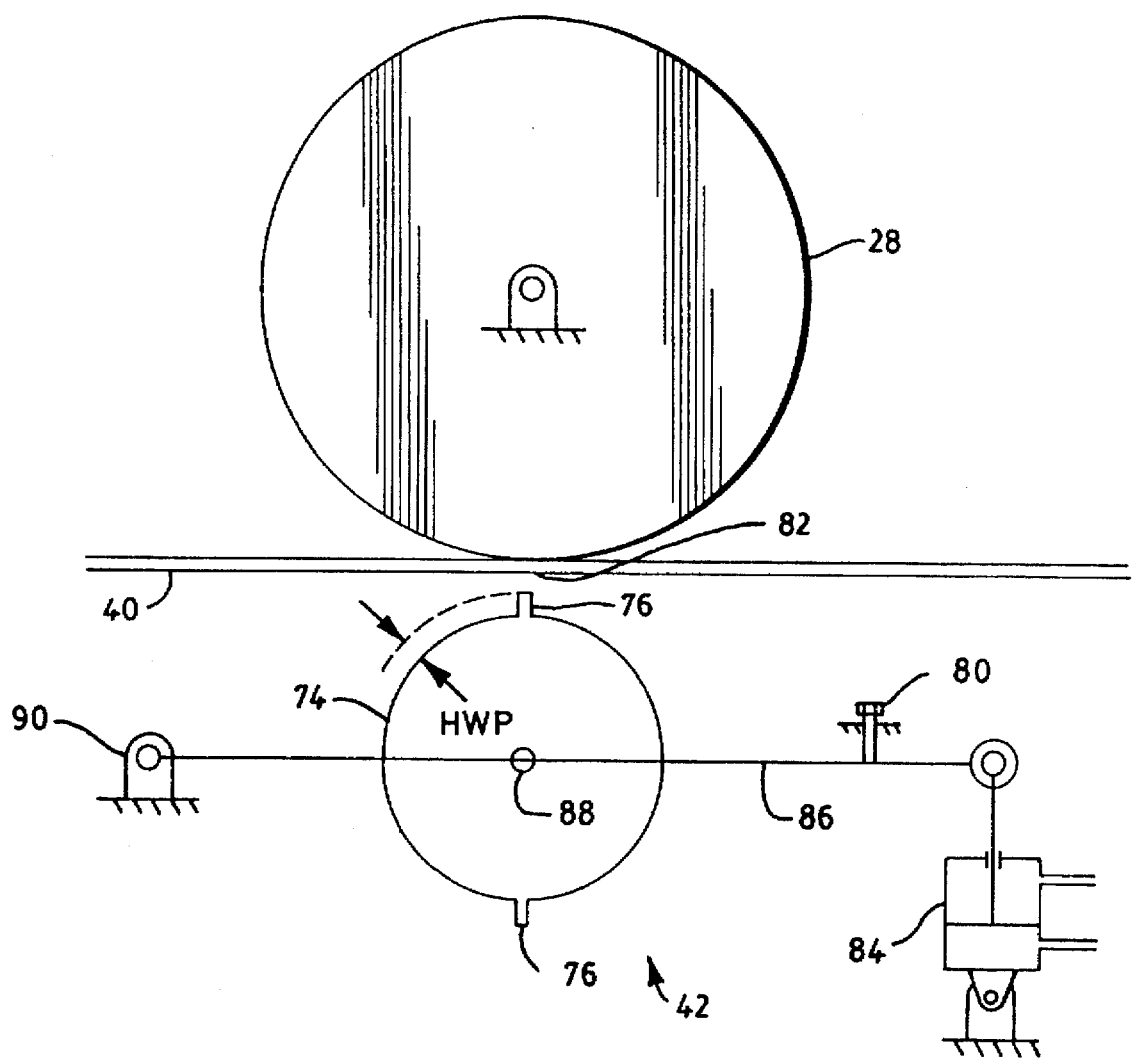
FIG. 11 is a side elevation of another embodiment of ultrasonic apparatus of this invention, showing apparatus for controlling nip engagement and nip pressures.

As illustrated by the combined showings of FIGS. 10 and 11, the absolute stop 80 spaces the outer radial surface of the anvil roll or horn carrying the working protuberance from the other element of activating member 75, whereby a gap 81 is maintained between the radial outer surface of the horn and the corresponding outer surface 83 of the anvil roll, whereby the outer radial surface 74 never comes into contact with the anvil roll 28; nor does the outer radial surface 74 exert any force against the combined web 40.

Similarly, the counterbalancing protuberance 78, when it approaches the area of nip 82, is spaced from the anvil by a distance corresponding to "HWP" minus "HCP," whereby the counterbalancing protuberance never comes into contact with, or exerts force on, the anvil roll 28. Thus counterbalancing protuberance 78 comprises a non-working counterbalancing protuberance.

So long as the thickness of the combined web 40 is less than the clearance between the counterbalancing protuberance and the anvil roll, the counterbalancing protuberance does not exert any force on the combined web 40. Where web thickness is greater than the clearance between the counterbalancing protuberance and the anvil roll, a substitute horn may be used, wherein the clearance between the anvil roll and the counterbalancing protuberance is greater than the thickness of the combined web 40.

In general, then, the working protuberance 76 rotates with the rotation of the rotary horn 42, thus temporarily closing the nip 82 once during each product repeat, for a period corresponding to the time required for the working protuberance to traverse the nip. The time "x" in seconds required for the working protuberance to transverse the nip is given by the equation $$x=(WWP/L)*T$$

where

L=Length of each workpiece, measured in the with machine direction

T=Time in seconds for each product to pass a given point in the process line.

For example, assuming a length "L" of 762 mm for each workpiece 19, a line speed of 10 products per minute (thus 6 seconds for each blank to pass any given point in the process line), and a width "WWP" of the working protuberance of 4.8 mm, the working protuberance traverses the nip, and is in working contact with each workpiece for 0.0375 seconds. Using the same equation, one can calculate the following relationships:

| Contact Time Seconds | Products Per Min. | Product Length, mm |
| --- | --- | --- |
| 0.0375 | 10 | 762 |
| 0.0038 | 100 | 762 |
| 0.0012 | 300 | 762 |
| 0.0006 | 600 | 762 |
| 0.1875 | 10 | 152 |
| 0.0188 | 100 | 152 |
| 0.0063 | 300 | 152 |
| 0.0031 | 600 | 152 |

In general, preferred dwell time corresponding to the time required for the working protuberance to traverse the nip 82 is between about 0.0005 second to about 0.20 second.

When the working protuberance 76 comes into contact with the combined web 40, and given the zero clearance setting of absolute stop 80, the thickness of the web 40 pushes the horn 42 and the anvil 28 apart against pressure being applied on the horn or anvil at nip 82. Referring to FIG. 11, a two way hydraulic cylinder 84 applies an upward force on anvil roll 28, through a rigid lever are bar 86 secured to the shaft 88 on rotary horn 42, which corresponds with the axis of rotation of the rotary horn 42. Rigid bar is secured to ground at fulcrum 90. In the inventors working examples, using e.g. 24 gsm spunbonded polypropylene webs and 940 decitex Lycra®, a nip pressure ranging from about 500 Newtons per Meter of linear contact, to about 9000 Newtons per Meter, is preferred.

Further to the operation of the ultrasonic horn, the amplitude of the horn vibrations is related to the structure and materials of each specific horn. Given a horn having an inner core member 68 structurally constructed as disclosed in U.S. Pat. No. 5,110,403 Ehlert, about 150 mm diameter, 50 mm width "WRS," of the outer radial surface, using a titanium alloy composition, a horn amplitude of about 0.025 millimeter to about 0.115 mm is typical. By increasing power input to the horn, amplitude can be increased somewhat to about 0.155 millimeter. But again, the amplitude range is generally limited by the structure of the horn used.

To control the amount of ultrasonic energy applied by the horn, one controls the combined factors of nip pressure, e.g. at nip 82, amplitude of the horn vibration, and the time for which the horn is in contact with the combined web 40. An increase in any one of the parameters, nip pressure, amplitude of horn vibration, and time of contact, increases the amount of energy applied.

As the amount of energy applied increases, so does the response of the materials in combined web 40. As minimal energy is applied, the ultrasonic apparatus may have no affect on the web. As the amount of energy input into the web at horn 42 is increased incrementally, the energy will eventually become large enough to cut the threads of elastic 112 while leaving only modest mark, if any, on a respective web 20, 30, or 32. As the energy input is increased further, the ultrasonic energy cuts the threads of elastic 112, and in the same operation forms a weld (not shown) between the base web 20 and the respective cover web 30, 32. If the amount of energy is further increased to a range above that preferred in this invention, the threads 112 are cut, along with cutting of base web 20 and the respective cover web 30, 32. Those skilled in the art will recognize that the specific parameters for achieving the above described levels of work depend on the apparatus used, the power inputted to the apparatus, and the characteristics of the combined web 40 being processed. Suitable ultrasonic generators are, of course, available from, for example, Branson Sonic Power Company, Danbury, Conn.

Figure 12:
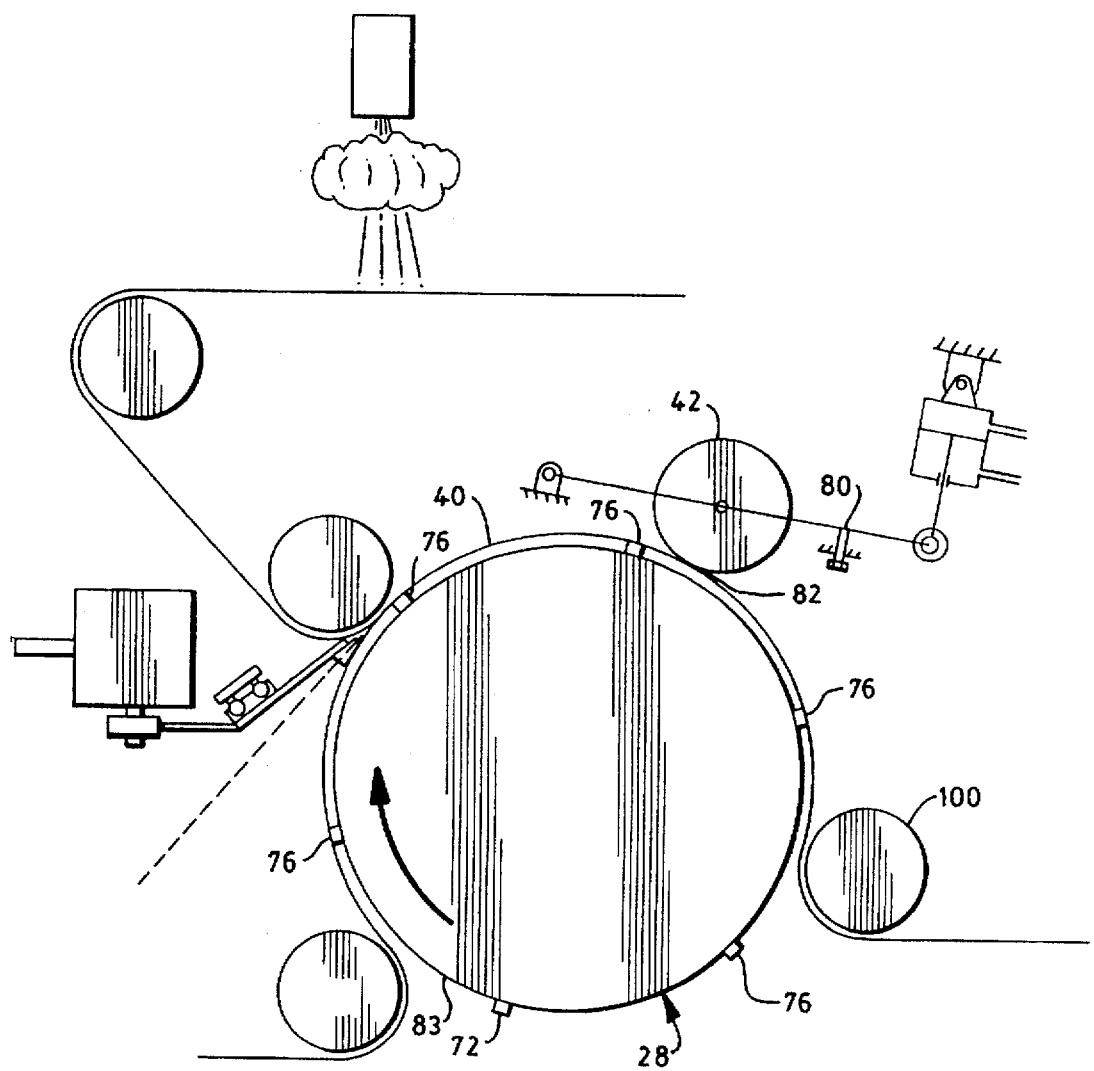
FIG. 12 is a side elevation of still another embodiment of the ultrasonics system of the invention.

While FIGS. 9 and 10 show one working protuberance and one counterbalancing protuberance, one can use more of each, as desired, with preference that the mass balance maintains the center of gravity at the axis of rotation 74. Accordingly, two working protuberances can be used wherein the second working protuberance replaces, and obviates the need for, counterbalancing protuberance 78. Thus, ultrasonic horn 42 can be free of nonworking or counterbalancing protuberances as shown in FIG. 11. Further, anvil roll 28 can support working protuberances 76 and be free of nonworking protuberances as shown in FIG. 12. The speed of rotation of the horn 42 is adjusted accordingly so that two workpieces 19 pass the horn for each rotation of horn 42.

The surface speed of the working protuberance 76 when in contact with the combined web 40 should match, preferably within about 10%, the surface speed of the web. However, in order that the working protuberance not operate on other areas of the web, the horn must advance rotationally only one, and exactly one working protuberance while the combined web 40 advances by the length of one workpiece. Since the circumference of the 150 mm diameter horn used as an example has a circumference of about 470 mm, and since the blank is typically 600–800 mm. long at length "L," the surface speed of the horn is reduced to below the constant surface speed of the combined web 40 while the horn is out of contact with the web. Accordingly, the speed of rotation of the horn is increased as the crotch portion 54 of a blank approaches the horn 42, matches the surface speed of web 40 as the working protuberance applies ultrasonic energy to the web 40 at crotch portion 54, and then is decreased after the crotch portion has passed the horn. One conventional method of controlling the rotational speed of the horn 42 is a servo motor (not shown). A preferred method of controlling the speed of rotation of the horn is to use a set of noncircular drive-gears 92, 94, shown illustratively in FIG. 3. A full disclosure of the structure and operation of such noncircular drive gears, to vary the speed of the driven device is given in copending application Ser. No. 08/186,352, herein incorporated by reference for its teaching of structure and use of noncircular gears.

It should be noted for completeness that a separate horn 42 is used at each inner edge 64 and 66 of the respective cover webs 30 and 32, as shown in FIG. 7.

The disclosure so far has focused on one or more working protuberances, disposed on the ultrasonic horn 42. FIG. 12 illustrates that the working protuberances can, in the alternative, be disposed on the anvil, whereupon a conventional ultrasonic horn e.g. as taught in U.S. Pat. No. 5,110,403 Ehlert can be used without modification. Referring to FIG. 12, a plurality of working protuberances 76 are disposed on outer surface 83 about the circumference of the otherwise conventional anvil roll 28, one working protuberance per repeat length of the product blanks being processed. A conventional rotating ultrasonic horn 42 is used to transfer ultrasonic energy to the web against the protuberances. Again, the absolute stop 80 is set for zero clearance between the horn and the anvil roll at each working protuberance 76. Accordingly, when the horn is not working against a protuberance 76, no pressure is exerted on the web 40, whereby minimal if any energy is transmitted from the horn 42 to the web between working protuberances.

FIG. 12 further illustrates an anvil roll 28, larger than the sonic horn 42, and carrying the working protuberances 76, whereby relative size of the horn and anvil, as well as the selection of which of the horn and anvil is to carry the working protuberance means, is a design choice.

As seen in FIGS. 11 and 12, where two or more working protuberances 76 are uniformly spaced about the circumference of the horn 42, or the anvil roll 28, no counterbalancing protuberance 78 is needed.

It is contemplated that the operation and functions of the invention have become fully apparent from the foregoing description of elements, but for completeness of disclosure, the usage of the invention will be briefly described.

Base web 20 is drawn into the processing elements shown, by the driving force on turning roll 26 against rotating anvil roll 28, and advances on the anvil roll 28 to the nip 62. At the same time, the cover webs 30 and 32 are drawn into the processing elements shown by the driving force of turning roll 38 at nip 62, passing first under adhesive spray 34 and over turning roll 36. Suitable adhesive for bonding e.g. the inventors' 24 gsm polypropylene spun-bonded webs is available as Findley H2096 hot melt adhesive, available from Findley Adhesives, Milwaukee, Wis. The adhesive spray is directed to cover the entire surfaces of webs 30 and 32, with exception of the edges in order to avoid adhesive overspray.

Threads of elastic are drawn into the nip 62 through thread guides 122. Guides 122 move transversely with respect to the machine direction of the advance of the webs 20, 30, and 32 along the processing-operation, in order to create the patterned paths 96 and 98 of the threads of elastic along the front and back portions 48, 50 of the leg openings 16.

The cover webs 30 and 32 are bonded to the base web 20 through the pressure at nip 62 in combination with the action of the adhesive layer 56, thus trapping the threads of elastic 112 between the base layer 20 and the respective cover webs 30, 32, except at the crotch portion 54 of each blank 18.

At each crotch portion 54, the threads of elastic 112 emerge from the edges of the adhesive layer 56, and cross the crotch portion along the inner edges 64 and 66 of the respective front and back cover webs. The portions of the threads of elastic 112C which cross the crotch portion 54 of the respective blanks 18 are cut by ultrasonic energy at sonic horn 42, without cutting the base web 20 or the respective cover web 30 or 32. However, the base web and cover webs could be cut by increasing the effective amount of power delivered to the web e.g. by increasing horn amplitude, contact time, and/or pressure at nip 82. The web, thus containing the so processed workpieces, leaves the anvil roll at turning roll 100 which is slightly spaced from the anvil roll 28. The blanks 18 can be cut from the continuous combined web 40 at any point after the crotch portions 112C of the elastic threads are cut. Thus, the blanks can be cut from the web by e.g. knife 102 on turning roll 100, and can be received on take away conveyor 104, as shown in FIG. 3. The workpieces may, of course, be further processed as a continuous web after leaving anvil roll 28 if desired, whereupon knife 102 would not be used at turning roll 100. Rather, a suitable knife would be applied at a location downstream from turning roll 100.

Reference is made to FIG. 1, wherein the garment includes, in addition to the leg elastics, waist elastics 106 and body elastics 108. The incorporation of the waist elastics 106 and body elastics 108 is done in conventional manner. Accordingly, these parts of the process are not shown, in the interest of simplicity.

While choosing not to be bound by any particular theory, the inventors believe that the discrete nature of the elastic threads, and perhaps the fact that their diameters differ from the general thickness of the webs 20, 30, and causes the threads 112 to concentrate the ultrasonic energy such that the threads respond to the ultrasonic energy before the base web or the cover webs respond. Thus, by limiting the amount of energy transmitted to the combined web 40, the effect is limited to that portion of the web (the threads of elastic) which responds first or, as desired, to a combination of cutting the threads of elastic and forming a weld between base web 20 and the corresponding cover web 30 or 32.

Having thus described the invention in full detail, it will be readily apparent that various changes and modifications may be made without departing from the spirit of the invention. All such changes and modifications are contemplated as being within the scope of the present invention, as defined by the following claims.

What is claimed is:

1. A rotary ultrasonic horn having an axis of rotation, said rotary ultrasonic horn comprising:
   (a) a first inner core member having the axis of rotation extending therethrough, said first inner core member having a circumference comprising a base diameter coincident with an outer radial surface extending about the circumference of said first inner core member, said outer radial surface having a width, said first inner core member having a center of gravity disposed at said axis of rotation; and
   (b) at least one working protuberance having a mass, and extending outwardly from said outer radial surface; and
   (c) at least one non-working counterbalance spaced from, and separate and distinct from, said working protuberance, said at least one non-working counterbalance being effective to counterbalance the mass of said working protuberance such that the center of gravity of the combination of said at least one working protuberance and said at least one non-working counterbalance is coincident with the axis of rotation.

2. A rotary ultrasonic horn as in claim 1, said at least one working protuberance extending outwardly from said outer radial surface a first distance comprising a first height and having a first width, said at least one non-working counterbalance extending outwardly from said outer radial surface a second distance comprising a second height and having a second width, said second height being smaller than said first height.

3. A rotary ultrasonic horn as in claim 1, said at least one working protuberance extending across up to the entire said width of said outer radial surface.

4. A rotary ultrasonic horn as in claim 2, said at least one working protuberance extending across the entire said width of said outer radial surface, said working protuberance having a substantially uniform cross-section across up to the entire said width of said outer radial surface.

5. A rotary ultrasonic horn as in claim 2, said base diameter of said first inner core member being about 100 mm to about 200 mm, said first height of said first working protuberance being about 0.5 mm to about 7 mm, said first width of said first working protuberance being about 0.5 mm to about 7 mm.

6. A rotary ultrasonic horn as in claim 4, said base diameter of, said first inner core member being about 100 mm to about 200 mm, said first height of said first working protuberance being about 0.5 mm to about 7 mm, said first width of said first working protuberance being about 0.5 mm to about 7 mm.

7. A rotary ultrasonic horn as in claim 2, said base diameter of said first inner core member being about 150 mm, said first height of said first working protuberance being about 4.8 mm, said first width of said first working protuberance being about 4.8 mm.

8. A rotary ultrasonic horn as in claim 3, said base diameter of said first inner core member being about 100 mm to about 200 mm, said first height of said first working protuberance being about 0.5 mm to about 7 mm, said first width of said first working protuberance being about 0.5 mm to about 7 mm.

9. A rotary ultrasonic horn as in claim 4, said base diameter of said first inner core member being about 150 mm, said first height of said first working protuberance being about 4.8 mm, said first width of said first working protuberance being about 4.8 mm.

10. An ultrasonics system, comprising:
   (a) an ultrasonic transducer, producing mechanical vibration at ultrasonic frequency;
   (b) a rotary ultrasonic horn connected to said ultrasonic transducer, and having a first axis of rotation, said rotary ultrasonic horn comprising a first inner core member having the first axis of rotation extending therethrough, said first inner core member having a first circumference comprising a base diameter coincident with a first outer radial surface extending about the circumference of said first inner core member, said first inner core member receiving mechanical ultrasonic energy from said ultrasonic transducer at the first axis of rotation, to thereby cause mechanical displacement of said rotary ultrasonic horn at an ultrasonic frequency, said first inner core member having a center of gravity disposed at said first axis of rotation; and
   (c) a rotary anvil having a second axis of rotation, a second circumference defining a second outer radial surface for receiving a workpiece to be worked by ultrasonic energy, and for cooperating with said rotary ultrasonic horn to form a close relationship comprising a gap between said rotary ultrasonic horn and said rotary anvil, said rotary ultrasonic horn further comprising at least one working protuberance extending outwardly from said outer radial surface, thereby to apply ultrasonic energy to a workpiece in the gap, said at least one working protuberance having a mass, said rotary ultrasonic horn including at least one non-working counterbalancing protuberance spaced from, and separate and distinct from, said working protuberance, said at least one non-working counterbalancing protuberance being effective to counterbalance the mass of said at least one working protuberance.

11. An ultrasonics system as in claim 10, said at least one working protuberance extending outwardly from said first outer radial surface a first distance comprising a first height and having a first width, said at least one non-walking counterbalancing protuberance extending outwardly from said first outer radial surface a second distance comprising a second height and having a second width, said second height being smaller than said first height.

12. An ultrasonics system as in claim 10, said first outer radial surface having a width, said at least one working protuberance extending across up to the entire said width of said outer radial surface.

13. An ultrasonics system as in claim 11, said first outer radial surface having a width, said at least one working protuberance extending across the entire said width of said outer radial surface, said working protuberance having a substantially uniform cross-section across up to the entire said width of said outer radial surface.

14. An ultrasonics system as in claim 11, said base diameter of said first inner core member being about 100 mm to about 200 mm, said first height of said first working protuberance being about 0.5 mm to about 7 mm, and said first width of said first working protuberance being about 0.5 mm to about 7 mm.

15. An ultrasonics system as in claim 13, said base diameter of said first inner core member being about 100 mm to about 200 mm, said first height of said first working protuberance being about 0.5 to about 7 mm, said first width of said first working protuberance being about 0.5 mm to about 7 mm.

16. An ultrasonics system as in claim 11, said base diameter of said first inner core member being about 150 mm, said first height of said first working protuberance being about 4.8 mm, said first width of said first working protuberance being about 4.8 mm.

17. An ultrasonics system as in claim 12, said base diameter of said first inner core member being about 100 mm to about 200 mm, said first height of said first working protuberance being about 0.5 mm to about 7 mm, said first width of said first working protuberance being about 0.5 mm to about 7 mm.

18. An ultrasonics system as in claim 13, said base diameter of said first inner core member being about 150 mm, said first height of said first working protuberance being about 4.8 mm, said first width of said first working protuberance being about 4.8 mm.

19. An ultrasonics system as in claim 10, said first outer radial surface extending continuously about the circumference of said first inner core member.

20. A rotary ultrasonics system, comprising:
(a) a rotary ultrasonic horn, having a first axis of rotation, and a first outer radial surface for applying ultrasonic energy to a workpiece to be worked; and (b) a rotary anvil having a second axis of rotation, a circumference including a base diameter and a second outer radial surface generally coincident with said base diameter for receiving a workpiece thereon and transporting the workpiece, and for cooperating with said rotary ultrasonic horn to apply energy to the workpiece being worked, said rotary anvil comprising at least one working protuberance on said second outer radial surface, extending outwardly from the base diameter, for working the workpiece using ultrasonic energy supplied by said ultrasonic horn, said rotary anvil including at least one non-working counterbalancing protuberance spaced from said at least one working protuberance.

21. A rotary ultrasonics system as in claim 20, said rotary anvil having a first length between first and second ends of said rotary anvil, said second axis of rotation extending in a direction coincident with the first length, said at least one working protuberance having a second length extending along the first length of said rotary anvil, said second length being shorter than said first length.

22. A rotary ultrasonics system as in claim 20, said rotary anvil having a first length between first and second ends of said rotary anvil, said second axis of rotation extending in a direction coincident with the first length, said at least one working protuberance having a second length, said at least one working protuberance having a cross section, substantially uniform along said second length.

23. A rotary ultrasonics system as in claim 21, said rotary anvil having a first length between first and second ends of said rotary anvil, said second axis of rotation extending in a direction coincident with the first length, said at least one working protuberance having a second length, said at least one working protuberance having a cross section, substantially uniform along said second length.

24. A rotary ultrasonics system as in claim 20, said at least one working protuberance having a height, measured from said second outer radial surface, of about 0.5 mm to about 7 mm, and a width of about 0.5 mm to about 7 mm.

25. A rotary ultrasonics system as in claim 21, said at least one working protuberance having a height, measured from said second outer radial surface, of about 0.5 mm to about 7 mm, and a width of about 0.5 mm to about 7 mm.

26. A rotary ultrasonics system as in claim 22, said at least one working protuberance having a height, measured from said second outer radial surface, of about 0.5 mm to about 7 mm, and a width of about 0.5 mm to about 7 mm.

27. A rotary ultrasonics system as in claim 23, said at least one working protuberance having a height, measured from said second outer radial surface, of about 0.5 mm to about 7 mm, and a width of about 0.5 mm to about 7 mm.

28. A processing system for processing workpieces in a continuous operation, said processing system comprising:
(a) an ultrasonic subsystem, said ultrasonic subsystem comprising (i) an ultrasonic transducer, (ii) a rotary ultrasonic horn connected to said ultrasonic transducer, and having a first axis of rotation, said rotary ultrasonic horn comprising a first inner core member having the first axis of rotation extending therethrough, said first inner core member having a first circumference comprising a base diameter coincident with a first outer radial surface extending about the circumference of said first inner core member, said first inner core member receiving ultrasonic energy from said ultrasonic transducer to thereby cause mechanical displacement of said rotary ultrasonic horn at ultrasonic frequency, said first inner core member having a center of gravity coincident with said first axis of rotation, and (iii) a rotary anvil having a second axis of rotation, a second circumference defining a second outer radial surface for receiving a workpiece to be worked by ultrasonic energy, and for cooperating with said rotary ultrasonic horn to form a close relationship comprising a gap between said rotary ultrasonic horn and said rotary anvil, said rotary ultrasonic horn further comprising at least one working protuberance extending outwardly from said outer radial surface, thereby to apply ultrasonic energy to a workpiece in the gap, said at least one working protuberance having a mass, said rotary ultrasonic horn further comprising at least one nonworking counterbalancing protuberance effective to counterbalance the mass of said at least one working protuberance such that the center of gravity of said rotary ultrasonic horn coincides with said first axis of rotation; and (b) apparatus for advancing a web, containing workpieces to be worked, through the gap at a first speed.

29. A processing system as in claim 28, including drive apparatus for driving, and thereby rotating, said rotary ultrasonic horn, and thereby substantially matching the surface speed of said working protuberance with said first speed when said working protuberance applies ultrasonic energy to the workpiece.

30. A processing system as in claim 29, said drive apparatus comprising a set of noncircular gears adapted to effect speed changes in said ultrasonic horn such that (i) the surface speed of said ultrasonic horn, substantially matches the surface speed of said rotary anvil while said working protuberance is applying ultrasonic energy to work the workpiece, and such that (ii) the surface speed of said ultrasonic horn substantially differs from the surface speed of said anvil while said working protuberance is not applying ultrasonic energy to the workpiece.

31. A processing system as in claim 30, said at least one working protuberance having a height, measured from said first outer radial surface, of about 0.5 mm to about 7 mm and a width of about 0.5 mm to about 7 mm.

32. A processing system, for processing a series of workpieces comprising garment-type products in a continuous web, said processing system including an ultrasonic subsystem for applying ultrasonic energy to effect physical change in workpieces in the continuous web, at periods spaced in time, and at discrete locations in the web, said ultrasonic subsystem comprising:

(a) an ultrasonic transducer producing mechanical vibration at ultrasonic frequency;

(b) a rotary ultrasonic horn connected to said ultrasonic transducer, and having a first axis of rotation, a first circumference comprising a base diameter coincident with a first outer radial surface, said first outer radial surface extending about the circumference of said ultrasonic horn;

(c) a rotary anvil having a second axis of rotation, a first length between first and second ends of said rotary anvil, a second circumference comprising a second base diameter coincident with a second outer radial surface for receiving workpieces to be worked by ultrasonic energy and for cooperating with said rotary ultrasonic horn to apply ultrasonic energy to workpieces to be worked by ultrasonic energy;

(d) one of said rotary ultrasonic horn and said rotary anvil having at least one working protuberance extending outwardly from the respective one of said first and second outer radial surfaces to form a close relationship comprising a gap between said rotary ultrasonic horn and said rotary anvil;

(e) apparatus for advancing the web, containing the workpieces, through the gap at a first speed; and (f) apparatus for effectively presenting said at least one working protuberance to each workpiece to be worked, to thereby close the gap to form a nip, apply ultrasonic energy to the workpiece, and correspondingly effect change in the workpiece, said working protuberance having a second length, shorter than the first length, said system being adapted to process a workpiece comprising first and second layers, a width, and an outer surface, the physical change comprising cutting the first layer without cutting any portion of any other layer of the workpiece.

33. A processing system as in claim 32, said system being adapted to process a workpiece comprising (i) a first layer, (ii) a second layer, and (iii) a width, said second length of said working protuberance being shorter than the width of the workpiece to be worked.

34. A processing system as in claim 32, said at least one working protuberance being disposed on said rotary ultrasonic horn, said processing system comprising drive apparatus for driving said rotary ultrasonic horn and thereby substantially matching the surface speed of said working protuberance with said first speed when said working protuberance applies ultrasonic energy to the workpiece.

35. A processing system as in claim 32, and including presenting said at least one working protuberance, intermittently, to each workpiece such that significant spaces exist, in successive workpieces, between areas of application of the ultrasonic energy.

36. A processing system as in claim 32, said at least one working protuberance having a height, measured from the corresponding said outer radial surface, of about 0.5 mm to about 7 mm, and a width of about 0.5 mm to about 7 mm.

37. A processing system as in claim 34, said at least one working protuberance having a height, measured from the corresponding said outer radial surface, of about 0.5 mm to about 7 mm, and a width of about 0.5 mm to about 7 mm.

38. A processing system as in claim 34, said at least one working protuberance having a height, measured from the corresponding said outer radial surface, of about 0.5 mm to about 7 mm, and a width of about 0.5 mm to about 7 mm.

39. A rotary ultrasonic horn having an axis of rotation, said rotary ultrasonic horn comprising:

(a) a first inner core member having the axis of rotation extending therethrough, said first inner core member having a circumference comprising a base diameter coincident with an outer radial surface extending about the circumference of said first inner core member, said outer radial surface having a width, said first inner core member having a center of gravity disposed at said axis of rotation;

(b) at least one working protuberance having a mass, and extending outwardly from said outer radial surface; and (c) at least one counterbalance spaced from, and separate and distinct from, said working protuberance, said at least one counterbalance being effective to counterbalance the mass of said working protuberance such that the center of gravity of the combination of said at least one working protuberance and said at least one counterbalance is coincident with the axis of rotation, said at least one working protuberance extending outwardly from said outer radial surface a first distance comprising a first height and having a first width, said at least one counterbalance extending outwardly from said outer radial surface a second distance comprising a second height and having a second width, said second height being smaller than said first height.

40. A processing system for processing workpieces in a continuous operation, said processing system comprising:

(a) an ultrasonic subsystem, said ultrasonic subsystem comprising (i) an ultrasonic transducer, (ii) a rotary ultrasonic horn connected to said ultrasonic transducer, and having a first axis of rotation, said rotary ultrasonic horn comprising a first inner core member having the first axis of rotation extending therethrough, said first inner core member having a first circumference comprising a base diameter coincident with a first outer radial surface extending about the circumference of said first inner core member, said first inner core member receiving ultrasonic energy from said ultrasonic transducer to thereby cause mechanical displacement of said rotary ultrasonic horn at ultrasonic frequency, said first inner core member having a center of gravity coincident with said first axis of rotation, and (iii) a rotary anvil having a second axis of rotation, a second circumference defining a second outer radial surface for receiving a workpiece to be worked by ultrasonic energy, and for cooperating with said rotary ultrasonic horn to form a close relationship comprising a gap between said rotary ultrasonic horn and said rotary anvil, said rotary ultrasonic horn further comprising at least one working protuberance extending outwardly from said outer radial surface, thereby to apply ultrasonic energy to a workpiece in the gap;

(b) apparatus for advancing a web, containing workpieces to be worked, through the gap at a first speed; and (c) drive apparatus for driving, and thereby rotating, said rotary ultrasonic horn, and thereby substantially matching the surface speed of said working protuberance with said first speed when said working protuberance applies ultrasonic energy to the workpiece, said drive apparatus comprising a set of noncircular gears adapted to effect speed changes in said ultrasonic horn such that (i) the surface speed of said ultrasonic horn substantially matches the surface speed of said rotary anvil while said working protuberance is applying ultrasonic energy to work the workpiece, and such that (ii) the surface speed of said ultrasonic horn substantially differs from the surface speed of said anvil while said working protuberance is not applying ultrasonic energy to the workpiece.

41. A processing system as in claim 40, said working protuberances having a mass, said rotary ultrasonic horn further comprising at least one counterbalancing protuberance effective to counterbalance the mass of said at least one working protuberance such that the center of gravity of said rotary ultrasonic horn coincides with said first axis of rotation.

* * * * *